United States Patent

Shimada et al.

[11] Patent Number: 4,478,217
[45] Date of Patent: Oct. 23, 1984

[54] LASER SURGICAL APPARATUS

[75] Inventors: Tamotsu Shimada, Akishima; Akio Kumada, Kokubunji; Daizo Tokinaga, Hachioji; Chiaki Shinbo, Mitaka; Hideyuki Horiuchi, Kokubunji; Masamoto Takatsuji, Tokyo, all of Japan

[73] Assignee: Hitachi, Ltd., Tokyo, Japan

[21] Appl. No.: 358,213

[22] Filed: Mar. 15, 1982

[30] Foreign Application Priority Data

Mar. 16, 1981 [JP] Japan ................................ 56-36623
Oct. 21, 1981 [JP] Japan ................................ 56-155478

[51] Int. Cl.³ .............................................. A61B 17/36
[52] U.S. Cl. ............................... 128/303.1; 116/205; 340/407
[58] Field of Search ............... 128/303.1, 305, 32, 128/24.1; 116/205; 340/407, 573, 566, 575; 331/64, DIG. 1

[56] References Cited

U.S. PATENT DOCUMENTS

| Re. 28,213 | 10/1974 | Kagan | 340/407 X |
| 2,284,040 | 5/1942 | Caldwell | 340/407 |
| 2,714,890 | 8/1955 | Vang | 128/305 |
| 2,754,505 | 7/1956 | Kenyon | 116/205 X |
| 3,035,133 | 5/1962 | Greenberg | 340/407 X |

Primary Examiner—John D. Yasko
Attorney, Agent, or Firm—Antonelli, Terry & Wands

[57] ABSTRACT

In a laser surgical apparatus having a laser oscillator operable to oscillate to produce a laser beam, and an optical path connected to the laser oscillator for transmission of the laser beam, a hand piece at the fore end of the optical path is equipped with a vibrator element comprised of a piezoelectric transducer, and the vibrator element applies a vibration to the hand piece.

16 Claims, 11 Drawing Figures

LASER SURGICAL APPARATUS

BACKGROUND OF THE INVENTION

This invention relates to a laser surgical apparatus for use in surgical operations.

In modern surgical operations in hospitals, so-called laser surgical knife apparatus utilizing a laser beam are taking the place of steel surgical knives which have long been used. FIG. 1 shows, in schematic form, a prior art laser surgical apparatus wherein a laser beam generated from a laser oscillator 1 is transmitted through an optical path 2 and irradiated on an affected part 4 by manipulating a hand piece 3 carrying the optical path in order to perform a surgical operation for incision and/or blood-coagulation.

For the laser surgical knife, a YAG (Yttrium Aluminum Garnet; $Y_3Al_5O_{12}$) laser or a carbon dioxide ($CO_2$) laser may be used. The former type laser generates a laser beam of a wavelength of 1.06 $\mu m$ and the latter type laser generates a laser beam of a wavelength of 10.6 $\mu m$, these wavelengths being invisible to naked eyes of the surgical operator. Accordingly, with the prior art laser surgical knife apparatus, the operator could not observe the emission of a laser beam from the forefront hand piece. Such a disadvantage is prone to an erroneous irradiation which may cause an erroneous operation or danger of the operator or the assistant operator, raising serious problems in securing safety in surgical operations. The operator often feels uneasy about these problems and cannot devote himself to an intended medical treatment.

In view of the above problems, use of laser surgical knife apparatus is regulated by the safety standard called ANSI (American National Standard Institute) Z 1361 - 1973. This standard rules that when operating a laser apparatus, an alert system using, for example, sound or alarm lamp should be used. Pursuant to this standard, it is possible to confirm whether the laser is emitting an invisible laser beam. To watch the alarm lamp, however, the operator must avert his eyes from the part to be operated and he cannot devote himself to the surgical operation. Also, the sound alert is generally noisy and may prevent proper communication of the operator's instructions to the assistant operator during the operation.

SUMMARY OF THE INVENTION

This invention contemplates elimination of the above disadvantages and has for its object to provide a laser surgical apparatus of which emission of laser can be readily confirmed by the operator thereby preventing erroneous irradiation of a laser beam to assure safe and steady operations.

To accomplish the above object, this invention has features in that means is provided for giving the operator vibratory sensation in response to emission of laser beam.

Specifically, according to the present invention, mechanical vibration is produced, in response to emission of a laser beam from a hand piece, to stimulate the operator.

DESCRIPTION OF PREFERRED EMBODIMENTS

Figure 1:
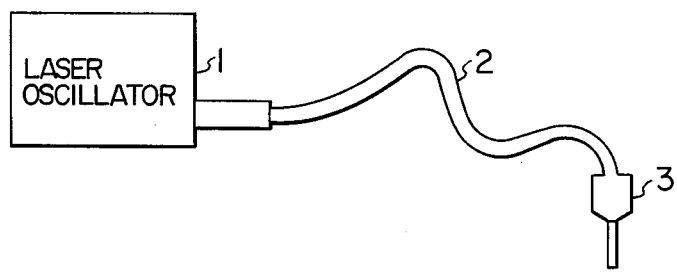
FIG. 1 is a schematic diagram illustrative of a prior art laser surgical apparatus.
Figure 2:
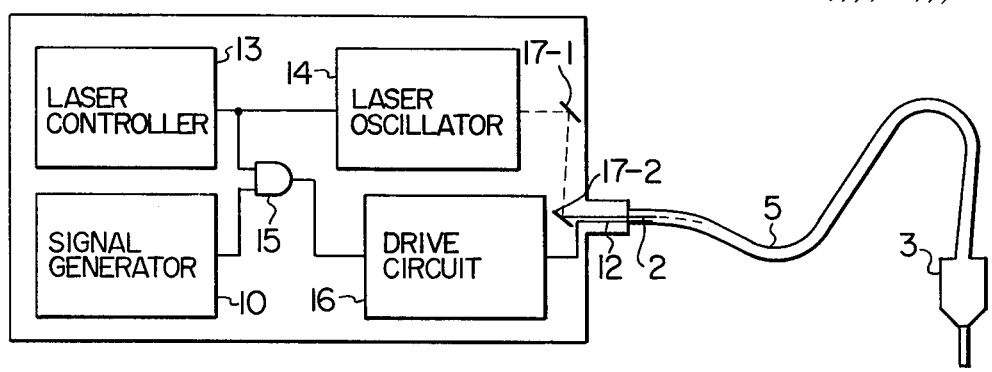
FIG. 2 is a diagram showing a construction of one embodiment of the invention.

Referring now to FIG. 2, there is shown a laser surgical apparatus embodying the invention. In the figure, a laser controller 13, a laser oscillator 14, and laser optical systems 17-1 and 17-2 constitute a laser unit of the laser surgical apparatus. The laser unit per se is conventionally known. A laser beam is emitted from the laser oscillator 14 controlled by the laser controller 13, and it is directed to an optical path 2 through the laser optical systems 17-1 and 17-2. On the other hand, a signal generator 10, an AND gate 15, a drive circuit 16 for driving a vibratory element (for example, a piezoelectric ceramic transducer) to be described later, and a signal line 12 constitute a vibration generator unit according to the present invention. The optical path 2 and the signal line 12 are inserted in a single cable 5. The output signal of the generator 10 is applied via the gate circuit 15 to the drive circuit 16 to generate a vibration signal. The vibration signal is transmitted to a hand piece 3 carrying the tip of the optical path 2 by way of the signal line 12. With this construction, the output signals of the laser controller 13 and the signal generator 10 are both applied to the AND gate circuit 15, so that the laser beam and the vibration signal are applied in synchronism relationship with each other, to the hand piece 3. As a result, the hand piece 3 vibrates only when the laser beam is emitting from the tip of the hand piece 3.

Figure 3:
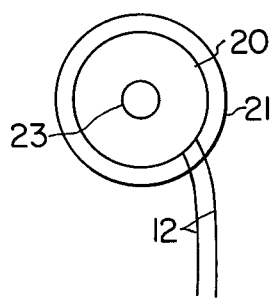
FIG. 3 is a diagram showing a construction of one example of a piezoelectric transducer used in the invention.

FIG. 3 is a plan view of a piezoelectric transducer used in the present invention and having a configuration adaptable to a cylindrical hand piece 3. The piezoelectric transducer as designated by reference numeral 20 is caused to vibrate by the vibration signal transmitted through the signal line 12. In order to propagate a vibration thus caused, the piezoelectric transducer 20 is surrounded by a vibration inducer 21 made of, for example, plastic. A central, small-sized hole 23 is provide to permit the laser beam to pass therethrough in the direction perpendicular to the transducer plane. The piezoelectric transducer may be of piezoelectric ceramics typically including so-called PZT ceramics such as lead titanate-zirconate ceramics, lead titanate ($PbTiO_3$) ceramics, and barium titanate ceramics.

Figure 4:
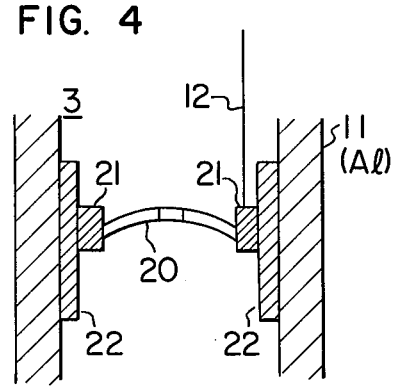
FIG. 4 is a diagrammatic representation showing an essential part of the invention.

The hand piece equipped with the piezoelectric transducer of FIG. 3 is best shown, in axial sectional form, in FIG. 4. In addition to the piezoelectric transducer 20 and the vibration inducer 21, another vibration inducer 22 and a side wall 11 of the hand piece 3 are seen in FIG. 4.

With this construction, the piezoelectric transducer 20, which is curved with its center portion projecting toward one side and fixed at its periphery to the vibration inducer 21, is driven by the signal on the signal line 12. In this case, the vibration-mode is a thickness vibration in which the vibration takes place in the axial direction. The vibration of the piezoelectric transducer is converted into a circurmferential (radial) vibration by the vibration inducer 21.

To put the hand piece in vibration over a wide area, the vibration inducer 22 made of, for example, aluminum is interposed between the side wall 11 of the hand piece and the vibration inducer 21.

When the thickness of the piezoelectric transducer to be used is large, the spherically curved transducer as shown in FIG. 3 may preferably be replaced by a flat and thick piezoelectric transducer. Since the thick piezoelectric transducer vibrates in radial mode, the provision of the vibration inducer 21 is not always necessary. In addition, if it is premised that the operator always grips the portion where the piezoelectric transducer is mounted when manipulating the hand piece 3, the vibration inducer 22 may also be eliminated.

The vibration inducers 21 and 22 are bonded together with adhesive, for example. The vibration inducer 22 may be fixed to the hand piece side wall 11 by screws or through threading.

The piezoelectric transducer 20 located as shown in FIG. 4 will be oscillated at a desired frequency by selecting the radius and thickness of the transducer. For example, with a piezoelectric transducer of 15 mm radius and 0.2 mm thickness, vibration frequencies of several of hundreds of $H_z$ can be obtained.

Figure 5:
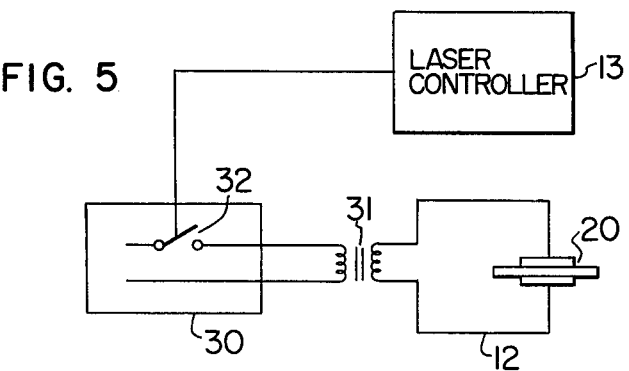
FIGS. 5 and 6 are circuit diagrams of drive circuits for the piezoelectric transducer.

The drive circuit 16 of FIG. 2 is exemplified in FIG. 5. As shown, a vibration signal generated from an oscillator 30 is coupled via an insulating transformer 31 and the signal line 12 to the transducer 20 for driving the same. The transmission of the vibration signal from the oscillator 30 is synchronized with the laser controller 13 by the aid of a switch 32 which is closed when the laser controller 13 is operating. For example, when the oscillation output of the oscillator 30 is determined by a voltage of 5 to 10 V and a current of 100 of 50 mA and the turn ratio of the insulating transformer is 1:5, the transducer 20 will start to oscillate with a voltage of 25 to 50 V and a current of 20 to 10 mA.

Figure 6:
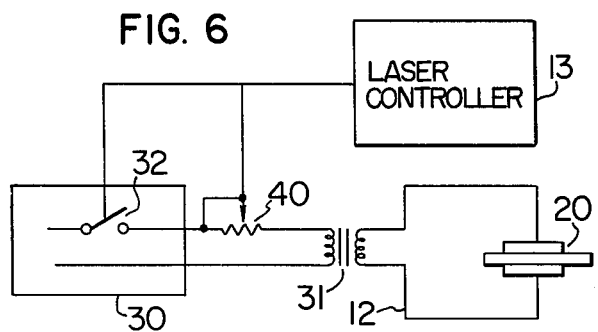

Another example of the drive circuit 16 is illustrated in FIG. 6 showing the same elements as those in FIG. 5 designated by the same reference numerals. This example features an additional variable resistor 40 which is responsive to the laser output of the laser controller 13 to vary the input voltage of the insulating transformer 31 so that the voltage being applied to the transducer 20 is varied in proportion to the laser output value. Consequently, variations in the laser output are converted into variations in the vibration level of the piezoelectric transducer for ultimate detection of a stimulus at the hand piece.

According to "Physiology of Sensation", Physiology Outline VI edited by Shinji Katsuki and published by Igaku Shoin, 1967, the minimum sensitivity of the human hand in sensing vibration corresponds to a vibratory deviation of 1 $\mu$m. The laser beam emitted from the laser surgical knife apparatus has a spot size of 100 to 200 $\mu m\phi$ and a proper value of the irradiation error due to the vibration of the hand piece is 10% of the laser beam spot size (10 to 20 $\mu$m). Accordingly, the voltage applied to the piezoelectric transducer is adjusted to 25 to 50 V so that the hand piece vibration is 1 $\mu$m at a minimum laser output of about 5 W and several of tens of microns at a maximum laser output of 50 W. Thus, for the vibration of the above order, the irradiation error of the laser beam emitted from the hand piece tip is negligible with respect to the affected part.

As described above, according to the invention, output conditions of the laser beam invisible to naked eyes can be transformed into stimuli to the hand of the operator and detected by the operator. With the laser surgical knife apparatus of the invention, safe and steady surgical operations can be achieved.

Although the vibration indicative of the laser beam emission is sensed by the palm of the hand of the operator in the foregoing embodiment, it may also be sensed by any of the back of the hand, the arm and the foot. Accordingly, the piezoelectric transducer may be adhered to the back of the hand or may be formed into a bracelet and put on the arm, for attaining the same effects as previously described. Further, the piezoelectric transducer may be carried on a foot switch attached to a conventional laser surgical knife apparatus and the vibration indicative of the laser beam emission may be sensed by the foot.

Figure 7:
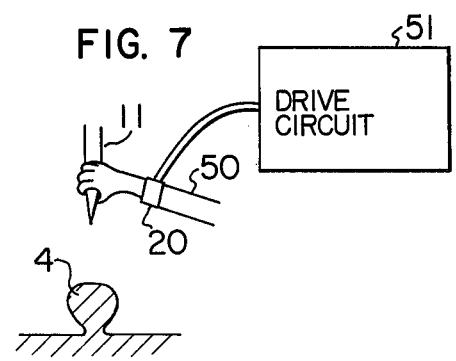
FIG. 7 is a diagram showing a construction of another embodiment of the invention.

FIG. 7 shows an example wherein a piezoelectric transducer 20 in the form of a bracelet is put on an arm 50 of the operator with the other elements remaining the same as in FIG. 2 and not illustrated. A drive circuit 51 for the transducer 20 is materialized with the circuit arrangement as shown in FIG. 5 or 6. With the construction shown in FIG. 7, a vibration responsive to the emission of a laser beam from the hand piece 3 is applied to the arm of the operator and the vibration indicative of output conditions of the invisible laser beam is sensed by the operator. This construction will therefore be advantageous for the operator who feels nervous about the vibration of the hand piece which dominantly affects sharpness of incision at an affected part 4.

In place of the piezoelectric transducer as described previously, a vibrator in the form of a known electromagnet with a coil may obviously be used.

Figure 8:
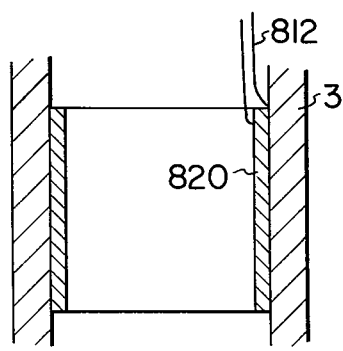
FIG. 8 is a diagram showing a construction of one example of a hollow pipe type piezoelectric transducer used in the invention.
Figure 9:
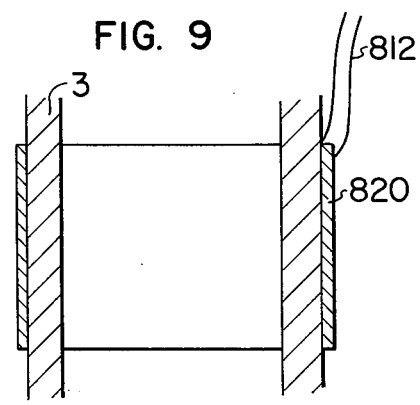
FIG. 9 is a diagram showing a construction of another example of the hollow pipe type piezoelectric transducer.

In the case of a cylindrical hand piece, a hollow pipe type piezoelectric transducer will preferably be used and mounted to the cylindrical hand piece as shown in FIGS. 8 and 9. In FIG. 8, a hollow pipe type piezoelectric transducer 820 is mounted on the inner wall of a hand piece 3 and in FIG. 9, a hollow pipe type piezoelectric transducer 820 is mounted on the outer wall of the hand piece 3. The transducer 820 as shown in FIG. 8 or 9 is caused to vibrate by a signal on a signal line 812.

Incidentally, as mentioned previously, the minimum sensitivity of the human hand in sensing vibration corresponds to 1 $\mu$m vibratory deviation, the spot size of the laser beam emitted from the laser surgical knife apparatus ranges from 100 $\mu m\phi$ to 200 $\mu m\phi$, and the vibration level of the hand piece will preferably be less than 10% of the laser beam spot size (10 to 20 $\mu$m) in consideration of both the minimum sensitivity of vibration and the allowable maximum irradiation error.

On the other hand, the variation level, $\Delta l$, of the hollow pipe type piezoelectric transducer can be calculated from the following equation:

$$\Delta l = d_{31} \frac{l}{t} V \qquad (1)$$

where
   $d_{31}$ : piezoelectric constant (m/V)
   l : pipe length
   t : thickness
   V : drive voltage.

For a piezoelectric transducer made of, for example, lead zirconium - titanate series, $d_{31} = -287 \times 10^{-12}$ (m/V). Assuming that l=40 mm, t=0.2 mm, and the drive voltage is 50 V, a vibration level of 6 μm is derived from equation (1). This vibration level is sufficient for the vibratory sensitivity and it does not adversely affect the irradiation error of the laser beam.

Figure 10:
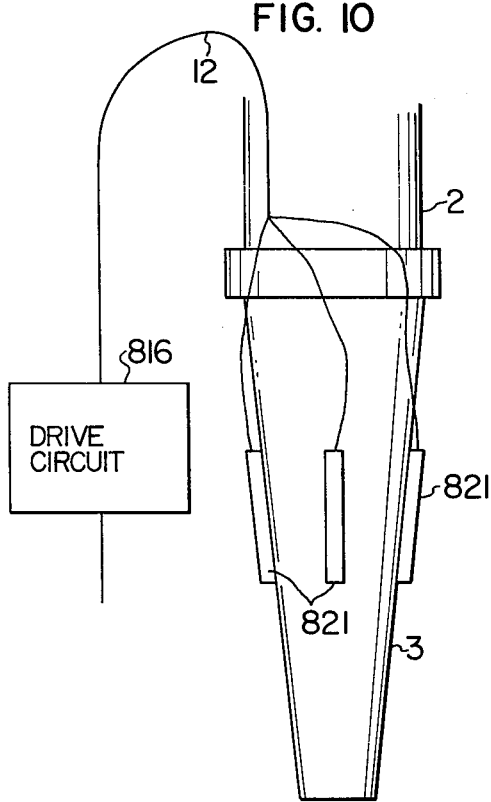
FIG. 10 is a diagram showing a construction of one example of a bimorph piezoelectric transducer.
Figure 11:
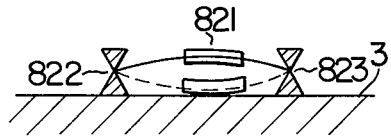
FIG. 11 is a diagram illustrative of a mounting structure of the bimorph piezoelectric transducer.

Turning to FIG. 10, a so-called bimorph cell or piezoelectric transducer formed of two piezoelectric elements put together is illustrated which is arranged according to teachings of the present invention. More particularly, bimorph piezoelectric transducers 821 are fixed with adhesive, for example, to a hand piece 3. The bimorph piezoelectric transducers are driven by a signal on a signal line 12 from a drive circuit 816. In order to ensure that fingers of the operator who grips the hand piece 3 never fail to come in contact with the transducers, these transducers are circumferentially distributed at an angular spacing of 90° as shown in FIG. 10. Due to the fact that the vibration level of the bimorph piezoelectric transducer is generally low, it is preferable in accordance with the invention that the transducer be mounted to the hand piece 3 in a manner as shown in FIG. 11. More particularly, opposite ends of an intervening bonding plate (metal plate) of the bimorph piezoelectric transducer 821 are fixed to support posts 822 and 823 which are fixed with adhesive to the hand piece 3. The support posts 822 and 823 are required to be electrically insulative and may preferably be made of bakelite or hard rubber. Advantageously, this arrangement can provide an optimum vibration level sensible by the operator and allows use of the reduced vibration frequency.

Obviously, the piezoelectric transducers 812 and 821 of FIGS. 8, 9 and 10 will be driven by the drive circuit as shown in FIG. 5 or 6 in the same manner as explained with reference to FIG. 5 or 6.

As has been described, the present invention ensures that the emission of the laser beam invisible to naked eyes can be transformed into stimuli to the hand of the operator and detected by the operator, thereby providing safe and steady surgical operations. This accounts for the following major advantages in the surgical operations:

(1) Erroneous irradiation is prevented to secure safety of the patient, operator and assistant operator;

(2) The operator can recognize the laser beam emission and devote himself to the intended operation;

(3) By making the laser output proportional to the stimulus to the hand, the operator can recognize the degree in sharpness of incision; and (4) An optimum vibration frequency can be selected in accordance with the sensitivity of stimulus of the hand of the operator.

The laser surgical apparatus described so far may be exclusively used for surgical operations in hospitals. However, laser apparatus of visible laser beam utilizing ruby (0.69 μm wavelength), helium - neon (0.63 μm), argon (0.45 to 0.51 μm) or krypton (0.47 to 0.64 μm) are used today in ophthalmology or dermatology. The visible laser beam cannot be recognized when irradiated on, for example, blackened skin cancer or the eyeground where blood vessels are explicitly seen. Accordingly, the vibrator of the present invention is also of great use in laser therapeutic apparatus for ophthalmology or dermatology utilizing visible laser beams.

What is claimed is:

1. A laser surgical apparatus comprising a laser oscillator operable to oscillate for producing a laser beam, an optical path connected to the laser oscillator for transmission of the laser beam and a hand piece connected to the optical path for irradiation of the laser beam onto an object, said hand piece being provided with vibration supply means for application of a vibration to said hand piece and including a piezoelectric transducer and vibration inducer means connected to said piezoelectric transducer, said vibration inducer means including a first vibration inducer for conversion of the vibration mode of said transducer and a second vibration inducer for transmission of a vibration from said first vibration inducer.

2. A laser surgical apparatus comprising a laser oscillator operable to oscillate for producing a laser beam, an optical path connected to the laser oscillator for transmission of the laser beam, and a hand piece connected to the optical path and manipulated for irradiation of the laser beam onto an object, detecting means for detecting emission of the laser beam, vibration supply means provided for the hand piece for application of a vibration thereto, and drive means responsive to the output of said detecting means to drive said vibration supply means.

3. A laser surgical apparatus according to claim 2, wherein said vibration supply means comprises a piezoelectric transducer.

4. A laser surgical apparatus according to claim 3, wherein said piezoelectric transducer is surrounded at its periphery by vibration inducer means.

5. A laser surgical apparatus according to claim 4, wherein said vibration inducer means comprises a first vibration inducer for conversion of the vibration mode of said transducer, and a second vibration inducer for transmission of a vibration from the first vibration inducer.

6. A laser surgical apparatus according to claim 1 wherein said piezoelectric transducer comprises a hollow pipe piezoelectric transducer.

7. A laser surgical apparatus according to claim 1 wherein said piezoelectric transducer comprises a bimorph piezoelectric transducer.

8. A laser surgical apparatus according to claim 3, wherein said piezoelectric transducer comprises a hollow pipe type piezoelectric transducer.

9. A laser surgical apparatus according to claim 3, wherein said piezoelectric transducer comprises a bimorph piezoelectric transducer.

10. A laser surgical apparatus comprising a laser oscillator operable to oscillate for producing a laser beam, an optical path connected to the laser oscillator for transmission of the laser beam, and a hand piece connected to the optical path for irradiation of the laser beam onto an object, and vibration means for indicating irradiation of the laser beam onto the object, said vibration means including vibration supply means for energization in synchronism with energization of said laser oscillator and for supplying vibration to said vibration means in synchronism with irradiation of the laser beam onto the object.

11. A laser surgical apparatus according to claim 10, wherein said vibration means is coupled to said hand piece for causing said hand piece to vibrate in synchronism with irradiation of the laser beam onto the object.

12. A laser surgical apparatus according to claim 10, wherein said vibration means includes means for coupling said vibration means to the operator of said hand piece for indicating to the operator the irradiation of the laser beam.

13. A laser surgical apparatus according to claim 10, wherein said vibration supply means has an energization value in dependence upon the laser beam value so that the vibration value of said vibration means varies in accordance with the laser beam value.

14. A laser surgical apparatus according to claim 10, wherein said vibration supply means includes means responsive to energization of said laser oscillator for energizing said vibration supply means in synchronism therewith.

15. A laser surgical apparatus according to claim 10, wherein said piezoelectric transducer comprises a hollow pipe piezoelectric transducer.

16. A laser surgical apparatus according to claim 10, wherein said piezoelectric transducer comprises a bimorph piezoelectric transducer.

* * * * *